(12) United States Patent
Lerner

(10) Patent No.: US 11,034,016 B2
(45) Date of Patent: Jun. 15, 2021

(54) EXOSKELETON DEVICE

(71) Applicant: Arizona Board of Regents on Behalf of Northern Arizona University, Flagstaff, AZ (US)

(72) Inventor: Zachary F Lerner, Flagstaff, AZ (US)

(73) Assignee: Arizona Board of Regents on Behalf of Northern Arizona University, Flagstaff, AZ (US)

( * ) Notice: Subject to any disclaimer, the term of this patent is extended or adjusted under 35 U.S.C. 154(b) by 81 days.

(21) Appl. No.: 16/409,670

(22) Filed: May 10, 2019

(65) Prior Publication Data

US 2019/0344433 A1   Nov. 14, 2019

Related U.S. Application Data

(60) Provisional application No. 62/670,465, filed on May 11, 2018.

(51) Int. Cl.
| | |
|---|---|
| *A61H 3/00* | (2006.01) |
| *B25J 9/00* | (2006.01) |
| *A61B 5/00* | (2006.01) |
| *A61B 5/103* | (2006.01) |
| *A61H 1/02* | (2006.01) |

(52) U.S. Cl.
CPC .......... *B25J 9/0006* (2013.01); *A61B 5/1038* (2013.01); *A61B 5/6829* (2013.01); *A61H 3/00* (2013.01); *A61B 5/4528* (2013.01); *A61B 5/4595* (2013.01); *A61H 1/0266* (2013.01); *A61H 2201/165* (2013.01); *A61H 2201/1642* (2013.01); *A61H 2201/5007* (2013.01)

(58) Field of Classification Search
CPC ... A61B 5/1038; A61B 5/6829; A61B 5/4595; A61B 5/4836; A61B 5/4851; A61H 3/00; A61H 1/0266; A61H 2201/1642; A61H 2201/165; A61H 2201/5007
See application file for complete search history.

(56) References Cited

U.S. PATENT DOCUMENTS

| | | | |
|---|---|---|---|
| 2003/0115031 A1* | 6/2003 | Dariush | G06F 19/3481 703/11 |
| 2004/0249316 A1 | 12/2004 | Ashihara et al. | |
| 2013/0226048 A1* | 8/2013 | Unluhisarcikli | A61H 1/00 601/34 |
| 2015/0321342 A1* | 11/2015 | Smith | B25J 19/005 74/490.03 |

(Continued)

*Primary Examiner* — Suba Ganesan
*Assistant Examiner* — Aren Patel
(74) *Attorney, Agent, or Firm* — Quarles & Brady, LLP

(57) ABSTRACT

A method of using an ankle exoskeleton device is provided herein. The method includes collecting one or more biomechanical data points from an individual. The method also includes developing individualized musculoskeletal simulations based on the one or more biomechanical data points. In addition, the method includes creating predictive simulations by modeling effects of an ankle exoskeleton device on the individualized musculoskeletal simulations. The method also includes utilizing established device-user relationships with real-time measurements to adjust device control. Lastly, the method includes optimizing design and control parameters of the exoskeleton device based on the predictive simulations and user responses.

16 Claims, 11 Drawing Sheets

(56) References Cited

U.S. PATENT DOCUMENTS

| | | | |
|---|---|---|---|
| 2016/0143800 A1* | 5/2016 | Hyung | A61H 1/0244 |
| | | | 623/32 |
| 2017/0202725 A1 | 7/2017 | Robertson et al. | |
| 2018/0177672 A1 | 6/2018 | Uchida et al. | |
| 2020/0039061 A1* | 2/2020 | Sankai | A61H 1/024 |

\* cited by examiner

EXOSKELETON DEVICE

CROSS-REFERENCE TO RELATED APPLICATION

This application claims priority to U.S. Provisional Application No. 62/670,465 filed on May 11, 2018, the entire contents of which is incorporated herein by reference.

FIELD OF THE INVENTION

The present disclosure generally relates to the field of rehabilitation robotics.

Specifically, the disclosure describes methods, implementations, and devices related to exoskeleton device gait rehabilitation.

BACKGROUND OF THE INVENTION

A number of injuries or conditions can lead to disorders that affect muscle control.

Individuals with muscle control disorders frequently experience a downward trend of reduced physical activity and worsening of gait function leading to a permanent decline in ambulatory ability. Accordingly, it is desired to develop methods, implementations, and devices for gait rehabilitation.

SUMMARY OF THE INVENTION

According to some aspects of the present disclosure, a method of using an ankle exoskeleton device is disclosed. The method includes collecting one or more biomechanical data points from an individual. The method also includes developing individualized musculoskeletal simulations based on the one or more biomechanical data points. The method further includes creating predictive simulations by modeling effects of an ankle exoskeleton device on the individualized musculoskeletal simulations. Lastly, the method includes optimizing design and control parameters of the ankle an exoskeleton device based on the predictive simulations.

In a further non-limiting embodiment of any of the foregoing and/or ensuing methods of using an ankle exoskeleton device, the method also includes determining an individual gait deficit of the individual by comparing the individualized musculoskeletal simulations to a simulation of a healthy individual.

In a further non-limiting embodiment of any of the foregoing and/or ensuing methods of using an ankle exoskeleton device, the design parameters include a control algorithm that utilizes data point from an embedded sensor on the exoskeleton device to track at least one data point, evaluates how the at least one data point changes over time, and adjusts a level of assistance provided by the exoskeleton device.

In a further non-limiting embodiment of any of the foregoing and/or ensuing methods of using an ankle exoskeleton device, the developing of individualized musculoskeletal simulations based on the one or more biomechanical data points utilizes wearable sensors or sensors embedded within the exoskeleton device.

In a further non-limiting embodiment of any of the foregoing and/or ensuing methods of using an ankle exoskeleton device, the developing individualized musculoskeletal simulations based on the one or more biomechanical data points includes determining an individual's gait deficits by comparing the results of the individualized musculoskeletal simulations to the data point collected on other individuals using the exoskeleton device.

In a further non-limiting embodiment of any of the foregoing and/or ensuing methods of using an ankle exoskeleton device, the method further includes collecting one or more biomechanical data points from an individual.

In a further non-limiting embodiment of any of the foregoing and/or ensuing methods of using an ankle exoskeleton device, optimizing design parameters of the exoskeleton device based on the predictive simulations further comprises augmenting existing muscle activity to elicit functional changes of the individual through activation of one or more actuators.

In a further non-limiting embodiment of any of the foregoing and/or ensuing methods of using an ankle exoskeleton device, the method further includes assisting the individual during a gait cycle through manipulation of the exoskeleton device.

In a further non-limiting embodiment of any of the foregoing and/or ensuing methods of using an ankle exoskeleton device, the method further includes resisting the individual during a gait cycle through manipulation of the exoskeleton device.

According to some aspects of the present disclosure, a wearable assistance system is provided herein that includes an ankle exoskeleton device comprising a control unit including a controller and a motor in electrical communication with the controller. The wearable assistance system also includes a measurement device configured to generate biomechanical data point of an individual. The measurement device is configured to determine an individual's gait deficits and the controller is configured to actuate the motor at an initial level of assistance based on the gait deficits.

In a further non-limiting embodiment of any of the foregoing and/or ensuing exoskeleton devices, the generated biomechanical data point of the individual is compared to a computer-generated model of a gait cycle.

In a further non-limiting embodiment of any of the foregoing and/or ensuing exoskeleton devices, the measurement device is a motion capture camera configured to detect movement and force gait analysis.

In a further non-limiting embodiment of any of the foregoing and/or ensuing exoskeleton devices, the measurement device utilizes a measurement of muscle activity through electromyography.

In a further non-limiting embodiment of any of the foregoing and/or ensuing exoskeleton devices, the measurement device utilizes a measurement of oxygen consumption/$CO_2$ production to determine a metabolic rate.

In a further non-limiting embodiment of any of the foregoing and/or ensuing exoskeleton devices, the actuator is operably coupled to a hinged assembly through a transmission assembly and configured to actuate the hinged assembly when the actuator is activated by the controller.

In a further non-limiting embodiment of any of the foregoing and/or ensuing exoskeleton devices, the hinged assembly includes an insole bracket rotatably coupled with an upright member.

According to some aspects of the present disclosure, a method of using an exoskeleton device is provided herein that includes collecting one or more biomechanical data points from an individual. The method also includes developing individualized musculoskeletal simulations based on the one or more biomechanical data points. The method further includes creating predictive simulations by modeling effects of an ankle exoskeleton device on the individualized musculoskeletal simulations. In addition, the method includes utilizing established biomechanical relationships governing the interaction between the device and the individual. Lastly, the method includes optimizing design or control parameters of the exoskeleton device based on the predictive simulations.

In a further non-limiting embodiment of any of the foregoing and/or ensuing methods of using an ankle exoskeleton device, the collecting one or more biomechanical data points from an individual includes utilizing motion capture of movement and force gait analysis via motion capture cameras utilizing on-board device sensors.

In a further non-limiting embodiment of any of the foregoing and/or ensuing methods of using an ankle exoskeleton device, the collecting one or more biomechanical data points from an individual includes utilizing a measurement of muscle activity through electromyography.

In a further non-limiting embodiment of any of the foregoing and/or ensuing methods of using an ankle exoskeleton device, the collecting one or more biomechanical data points from an individual includes utilizing a measurement of oxygen consumption/CO2 production to determine a metabolic rate.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 3:
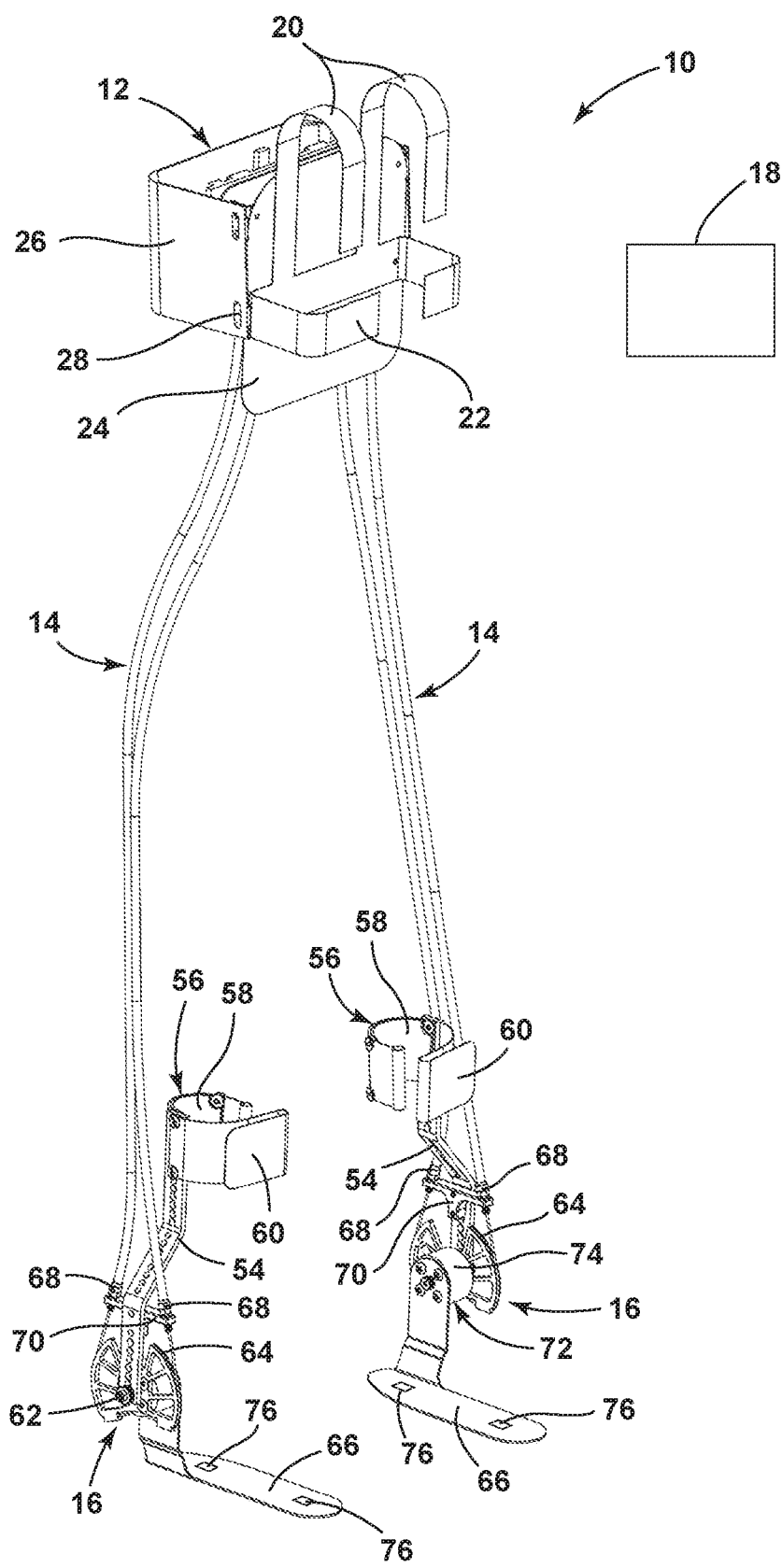
FIG. 3 is a front isometric view of a wearable exoskeleton device; according to some embodiments.
Figure 4:
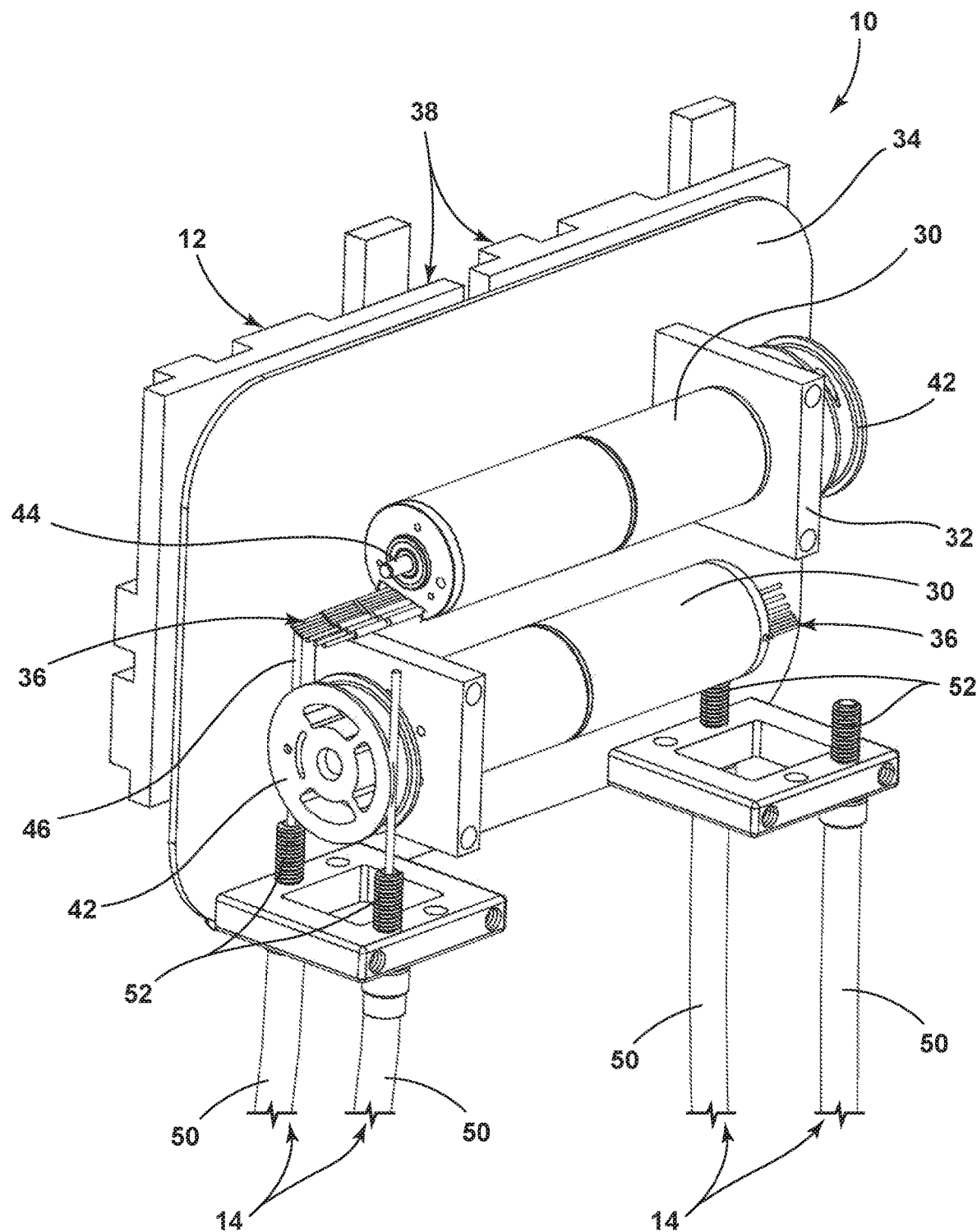
FIG. 4 is a front isometric view of a control unit of the exoskeleton device of FIG. 3, according to some embodiments.
Figure 5:
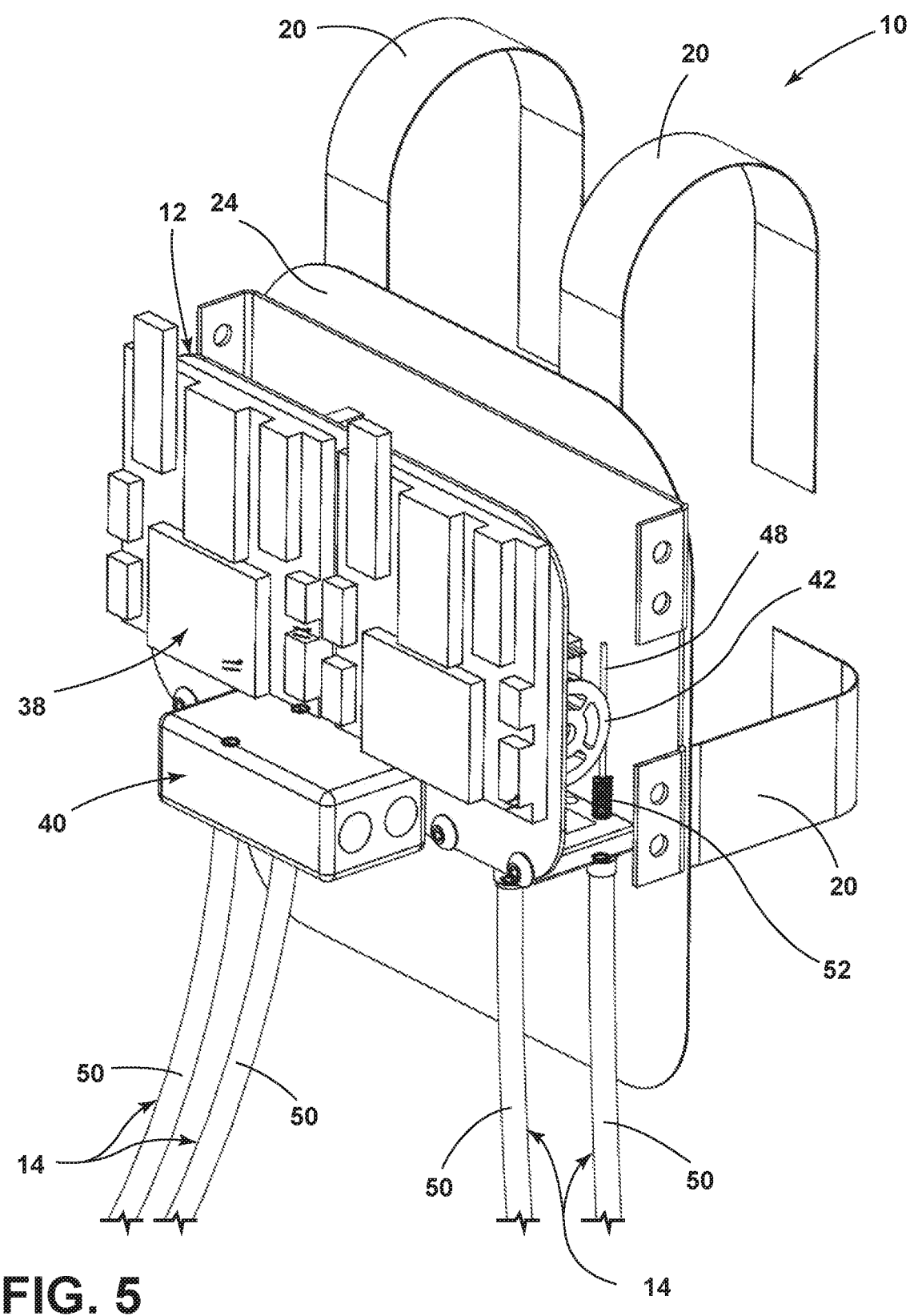
FIG. 5 is a rear isometric view of the exoskeleton device of FIG. 3, according to some embodiments.
Figure 6:
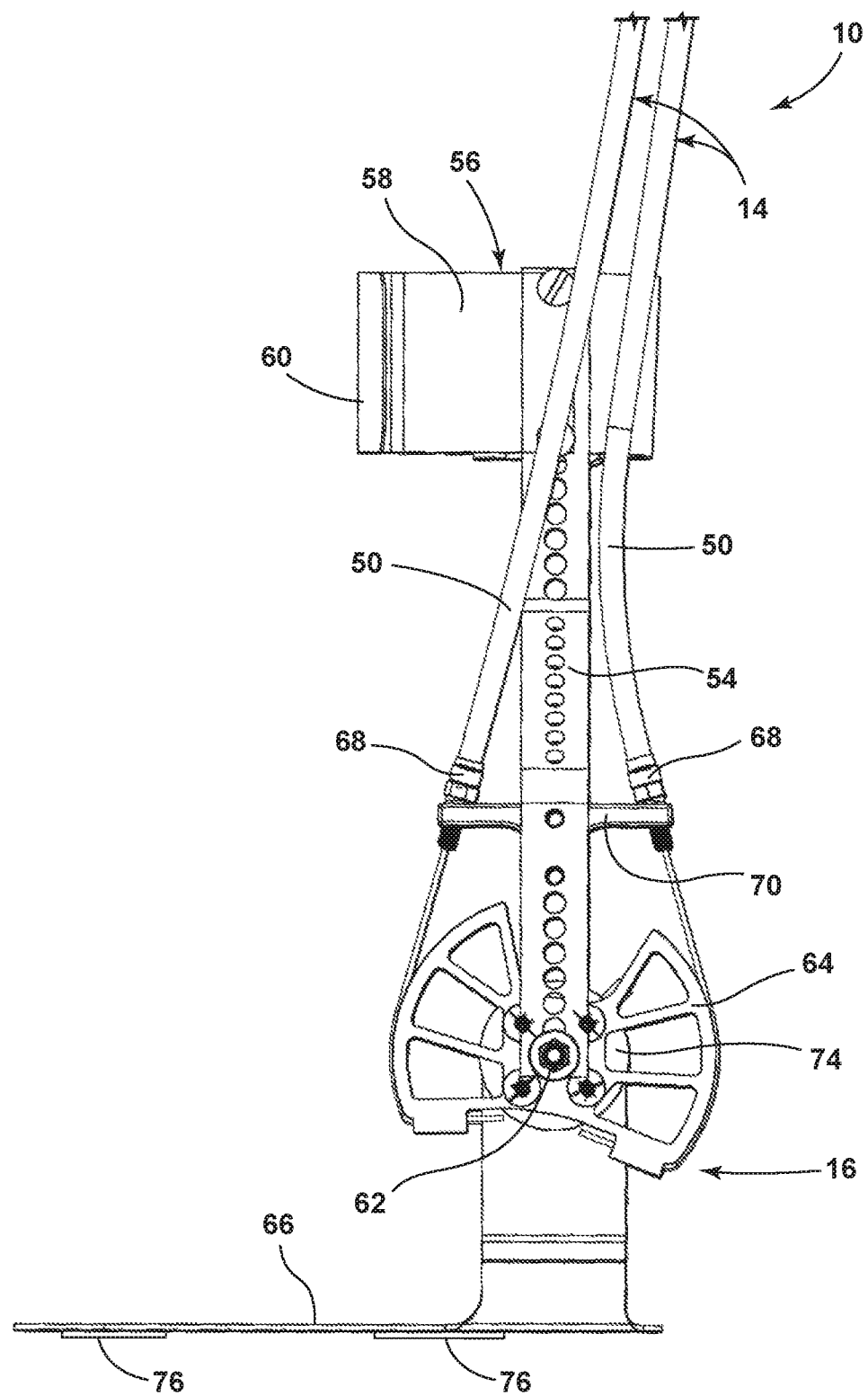
FIG. 6 is a side plan view of a lower hinged assembly that is operably coupled with the control unit through a transmission assembly, according to some embodiments.

For purposes of description herein, the terms "upper," "lower," "right," "left," "rear," "front," "vertical," "horizontal," and derivatives thereof shall relate to the embodiment of the invention as oriented in FIG. 3. However, it is to be understood that the invention may assume various alternative orientations, except where expressly specified to the contrary. It is also to be understood that the specific devices and processes illustrated in the attached drawings, and described in the following specification are simply exemplary examples of the inventive concepts defined in the appended claims. Hence, specific dimensions and other physical characteristics relating to the examples disclosed herein are not to be considered as limiting, unless the claims expressly state otherwise.

As required, detailed examples of the present invention are disclosed herein. However, it is to be understood that the disclosed examples are merely exemplary of the invention that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present invention.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items can be employed. For example, if any assembly or composition is described as containing components A, B, and/or C, the assembly or composition can contain A alone; B alone; C alone; A and B in combination; A and C in combination; B and C in combination; or A, B, and C in combination.

As used herein, the terms "assistance" and "resistance" may be used interchangeably to signify the direction of external torque applied to a joint that may be perceived as augmenting (making a movement easier, assistance) or harder (resistance).

Neurological deficits, such as those caused by stroke, spinal cord injury, and cerebral palsy, often lead to reduced walking ability and gait patterns that limit quality of life. Achieving and maintaining independent mobility for the estimated 17 million individuals with walking disabilities in the U.S. is a rehabilitation challenge. Currently, standard-of-care treatments are not fully effective in restoring gait function. Physical therapy, treadmill-based gait training, and intensive muscle strengthening programs have demonstrated variable and often minimal success for gait rehabilitation. Research suggests that the type and dosage of standard therapy programs are insufficient for large sustainable gains.

Figure 1:
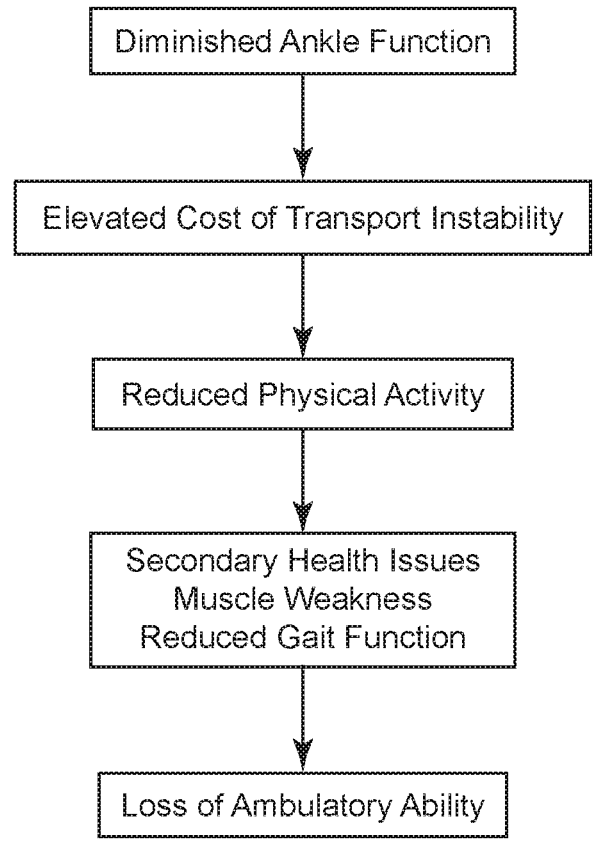
FIG. 1 is a flowchart of a natural progression of ambulatory decline in individuals with various gait disorders.
Figure 2:
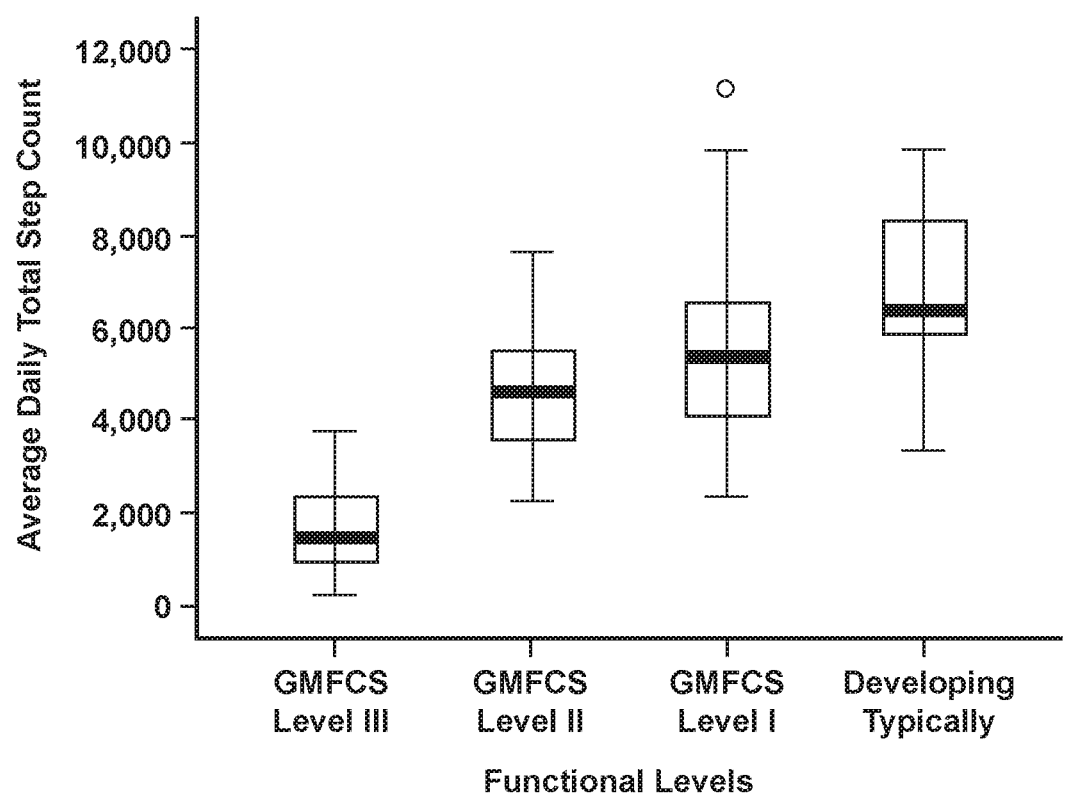
FIG. 2 is a graph of the differences in daily total step count by various persons having cerebral palsy (CP) at various functional levels.

FIG. 1, for example, depicts a sequence of events that can ultimately lead to loss of ambulatory ability. Specifically, in some individuals, diminished ankle functionality results from lack of muscle strength and can lead to elevated energy costs associated with transport that, in turn, leads to reduced physical activities. The reduced physical activities lead, in turn, to secondary health issue, muscle weakness, and reduced gait function leading to loss of ambulatory function. FIG. 2 is a chart depicting reductions in steps taken for individuals having muscle control disorders as compared to individuals without muscle control disorders according to some examples. For children with cerebral palsy (CP), for example, walking can be drastically more energetically expensive than for their typically developing peers. Muscle strength and endurance do not increase in proportion to body mass during growth, which can contribute to declining walking ability. The ability to walk is related for physical health and general well-being across the life-span. Reduced level of weight-bearing physical activity contributes to a wide range of secondary conditions associated with CP, such as metabolic dysfunction, cardiovascular disease, fatigue, weakness, osteoporosis, and chronic pain.

Robotic-assisted gait rehabilitation has grown in application for neurological conditions, however, results of laboratory-based robotic treatments on gait recovery vary. Wearable assistive devices (i.e. powered orthoses) offer potential improvements in gait rehabilitation outcomes and meet the increasing demand for therapy from the aging U.S. population.

Despite the potential for exoskeleton devices to revolutionize gait rehabilitation, there are several remaining challenges that must be addressed, particularly in regards to how they interact with the user. For example, most exoskeleton devices have not been specifically designed to engage the user, and have therefore been largely unsuccessful in improving outcomes over traditional therapies. In other words, existing exoskeleton device control strategies are not tailored to the individual, nor encourage active participation. To improve efficacy, exoskeleton device assisted rehabilitation will benefit from increased active engagement during task-specific training. Enhancing user engagement during robot-assisted tasks can be improved by tracking user performance over-time and providing real-time performance feedback.

Additionally, current rehabilitation techniques for stroke survivors and patients with Parkinson's disease are insufficient in effectively restoring gait function. New treatment strategies are needed that will allow for increased dosage of targeted therapy. Recently, it has been demonstrated that repeated cadence training via stationary cycling machines can improve gait and other functional outcomes in these patient populations. The various embodiments of this disclosure, combined with advances in electromechanical actuation, offers the potential for implementing similar task-specific training via light-weight robotic devices that can be worn by patients outside of the laboratory. Further, musculoskeletal models can identify the underlying mechanisms of an individual's gait deficit and may be used to provide targeted robotic rehabilitation that improves outcomes.

By improving walking economy, individuals with gait deficits may engage in greater amounts of habitual physical activity. This may prolong walking ability and have many additional physical and mental health benefits, such as increasing muscle and bone mass. Additionally, increased daily activity would likely also have rehabilitation related benefits, including maintenance or improvement of baseline walking ability, by increasing muscle strength and coordination.

The following disclosure describes device and methods of utilizing the exoskeleton device to provide powered assistance designed to increase mobility or facilitate rehabilitation in a user. The powered exoskeleton device is a wearable, mobile device that allows a user to perform limb motions with additional external power, for increasing a user's strength or endurance. The powered exoskeleton device may operate specifically to facilitate rehabilitation, providing resistance for targeted and functional strengthening. The device may also operate specifically to increase mobility, providing assistance, aim to enhance or augment the user's capabilities. The exoskeleton device may be used during daily life and may offer a transformative new option for improving mobility by reducing barriers to physical activity, such as for individuals with neurologically-based gait disorders. The barriers to mobility faced by individuals (e.g. individuals with gait deficits) may include prohibitively high metabolic cost of transport and difficulty completing strength- and balance-intensive weight-bearing tasks such as navigating stairs and around or over obstacles. For improving gait mechanics and walking efficiency, robotic joint (e.g. ankle, knee, hip, and/or any other joint) actuation can provide positive power to the body through appropriately-timed assistance (e.g. extension/contraction assistance). For increasing functional strength, robotic joint actuation may resist a movement or targeted muscle group, including powered resistance that is proportional to the instantaneous demand on the joint (i.e. net muscle moment).

The wearable exoskeleton device offers new methods for improving walking ability. For example, the exoskeleton device provided herein may include techniques (e.g. real-time biofeedback) to encourage favorable changes in volitional muscle activity patterns.

The ankle joint plays a critical role in whole-body stability and forward propulsion during walking. Dynamic ankle actuation and stability control are required for independent and effective function at home and in the community. Assistance at or near the ankle joint appears to provide improvement in walking economy and has the potential to reduce the metabolic cost of transport. Likewise, dynamic or intermittent actuation and stability of a knee joint can also be required, which may be improved by providing assistance at or near the joint. Other movements of the body may likewise be improved by providing assistance near various other joints of the body. This type of powered assistance may seek to maintain and ultimately augment the wearer's range of motion and muscle strength. Furthermore, by offering the potential to reduce the metabolic cost of activity (e.g. walking), powered joint assistance may lead to increases in habitual physical activity.

In some embodiments, for improving gait mechanics and walking efficiency, robotic actuation can provide positive power to the body through appropriately-timed assistance (e.g. plantar-flexion assistance) during the walking process.

For improving performance during balance-intensive tasks, an exoskeleton device (e.g. an ankle exoskeleton device) can respond rapidly to perturbations or abrupt changes in posture by modulating joint torque, and therefore joint impedance, in real-time, to help maintain balance.

In some embodiments, the present exoskeleton device may provide assistance during some modes of operation intended to improve mobility or posture in the form of linear force and/or rotational force (i.e. torque). Alternatively, the exoskeleton may provide resistance a mode of operation designed to increase muscle recruitment during a function task (e.g. walking) in the form of linear force and/or rotational force (i.e. torque). The assistance or resistance may be provided to various hinged assemblies of the exoskeleton device. The electronic assistance may be provided by a powered ankle-foot orthosis (AFO), a knee assembly, and/or any other joint assembly that is coupled with a control unit through a transmission assembly. For example, FIGS. 3-6 illustrate various embodiments of the exoskeleton device 10 that includes a control unit 12, a transmission assembly 14, and a pair of hinged assemblies 16. In the illustrated embodiment, the exoskeleton device 10 includes two lower hinged assemblies 16 for a right foot and a left foot of a user. Each of the lower hinged assemblies 16 is configured as an AFO.

In some embodiments, the exoskeleton device 10 may also include a feedback modality 18 for providing feedback regarding the individual's use of a wearable exoskeleton device 10 in a free-living environment. In some instances, a method for providing feedback to an individual using a prosthesis utilizes a computer monitor mounted at line-of-sight in front of a treadmill that provides a near real-time visual display of desired biomechanical parameters and the individual's compliance or non-compliance with these parameters. However, as can readily be determined, this type of feedback can be incompatible with use outside of a rehabilitation facility and in free-living settings. Accordingly, in some embodiments, the exoskeleton device 10 may utilize other methods for providing feedback that include auditory feedback via speakers or headphones or earbuds, vibrotactile feedback via small vibration actuators, and/or wearable visual feedback via body-warn displays (e.g. wrist mounted monitor or LEDs).

In the embodiment illustrated in FIGS. 3-6, the control unit 12 includes attachment straps 20 used to attach the control unit 12 to an individual or a user (e.g. along a user's back). In some examples, the straps 20 may include first and second vertical straps along with a waist strap. Any of the straps 20 may be attached to one another on one or both end portions thereof. Moreover, the waist strap may include a buckle 22 that allows for engagement of two end portions of the strap and adjustability as to the length of the strap 20. The straps 20 may be flexible or rigid. The attachment straps 20 may additionally or alternatively be of a waist strap form, a backpack form, or any other structure for supporting weight on the user's waist, torso, or other attachment site.

In the embodiment of FIGS. 3-6, the attachment straps 20 are operably coupled to a base plate 24. The base plate 24 may provide a surface for mounting or supporting components of the control unit 12 such as a housing shell 26, which may serve to cover or protect internal components of the control unit 12 from direct view or interference. The housing shell 26 may include be formed from covering material (e.g. plastic, aluminum, cloth) suitably arranged to cover the control unit 12 and can have any design disposed thereon. The base plate 24 may be coupled to the housing shell 26 by a plate-to-housing attachment feature 28. This plate-to-housing attachment feature 28 may include correspond engagement features and/or removable fasteners, with examples including bolts, magnets, clips, and slots. In some embodiments, the base plate 24 and the housing shell 26 may be embodied as an integral component, which may include a single piece or multiple pieces.

The control unit 12 may include one or more actuators 30 that can be supported on the actuator base plate 24. The one or more actuators 30 may generate force through a rotary electric motor, linear electric motor, hydraulic piston, pneumatic piston, pneumatic bladders, combinations thereof, and/or any other device capable of generating a force. The one or more actuators 30 are coupled to the base plate 24 through one or more brackets. The one or more actuator brackets 32 may be formed from a metallic, polymeric, or other suitable material for securing the one or more actuators 30 to the base plate 24. A top plate 34 may be positioned on an opposing side of the one or more actuators 30 from the base plate 24. The one or more actuator brackets 32 may attach to the base plate 24, the one or more actuators 30, or to the top plate 34 through removable or non-removable fasteners (e.g., bolts, clips, slots).

Actuator wiring 36 may electrically couple with the one or more actuators 30 and is configured to carry electrical power or electrical control signals to and from the one or more actuators 30 to a circuit board 38 and/or components thereof. The one or more circuit boards 38 may include one or more printed circuit boards (PCBs), mounting one or more circuits or chips, for performing one or more functions described herein. The one or more circuit boards 38 may be removably or non-removably coupled to the top plate 34 through fasteners, such as bolts, clips, slots, or other fasteners. In an alternate embodiment, the one or more circuit boards 38 may be coupled to one or more other components within the control unit 12.

The circuit board can include various electrical components, such as memory, processors, controllers, transceivers, and/or any other device. The various electrical components may have power supplied thereto by one or more batteries that are also supported by the control unit. For example, in the embodiment illustrated in FIGS. 3-6, one or more batteries 40 are coupled to the top plate 34, to the circuit board 38, or to any other component of the control unit 12 by removable or non-removable attachments (e.g. brackets or bolts). The one or more batteries 40 may be any device capable of storing and delivering electrical power, with examples including nickel cadmium, nickel metal hydride, lithium ion, lead acid, alkaline, lithium batteries, and so on. The one or more batteries 40 may be rechargeable or single use. The control unit 12 may further include circuitry and components for connecting and rectifying external electrical power received from external sources to recharge the one or more batteries 40, in some embodiments.

The first actuator can include a first shaft extending therefrom and the second actuator includes a second shaft extending therefrom, the first and second shafts extending in substantially opposing directions within the control unit. Each actuator can be coupled to one or more pulleys or other devices for assisting in translating movement of the actuator to a movement in a different direction. For example, in the embodiment illustrated in FIGS. 3-6, one or more actuator pulleys 42 are double-wrap side-hole pulleys. The pulleys 42 are generally axially aligned with a shaft 44 of the actuator 30 and rotates in conjunction with each respective actuator 30. In some embodiments, the one or more actuator pulleys 42 may be any suitable device for transferring force from the one or more actuators 30 to a transmission assembly 14.

The force generated by the one or more actuators can be carried by one or more transmission elements of the transmission assembly. The transmission elements are configured to provide force to various elements of the exoskeleton device that can be remote from the control unit. For example, cams, linear shafts, pistons, universal joints, and other force-transferring linkages may be implemented. In embodiment illustrated in FIGS. 3-6, the transmission assembly 14 includes one or more extension cables 46 and one or more contraction cables 48. The extension cables 46 and contraction cables 48 may be arranged to transfer opposing forces due to the suitability of cables for transferring "pulling" forces but not for transferring "pushing"

forces. In some embodiments, a single transmission element may be used to transfer opposing (both pushing and pulling) forces.

In the embodiment of FIGS. 3-6, the transmission assembly 14 is routed down one or more legs of a user to reach the lower hinged assembly 16. In the illustrated example, the transmission assembly 14 is lightweight and flexible so as to allow minimal impediment of motion of the knee and hip joints of a user. The AFO may include one or more lubricating fluids or materials, disposed on an element or between two relatively-moving elements to reduce friction and increase efficiency. The extension cables and contraction cables may be formed from any suitable material, with examples including metal, Kevlar, and nylon.

The one or more extension cables and one or more contraction cables may each be housed in a cable sheath. The one or more cable sheaths may serve to support and house the extension cables and contraction cables. In the embodiment illustrated in FIGS. 3-6, the extension cables 46 and contraction cables 48 may be Bowden cables that transfer force via the movement of inner cables relative to a hollow sheath 50 or housing containing the inner cable. The one or more cable sheaths 50 may each be coupled to barrel adjustors 52. The barrel adjustors 52 allow for adjustment of the length of the sheaths 50 to adjust a baseline tension of the extension cables 46 or contraction cables 48. The one or more barrel adjustors 52 may be further coupled to the one or more cable brackets.

In the embodiment illustrated in FIGS. 3-6, each lower hinged assembly 16 includes an upright member 54 that serves as a mounting or support element for the components of the lower hinged assembly 16. Each upright member 54 may be additionally coupled to an orthotic cuff 56. The orthotic cuff 56 may be additionally coupled to a D-ring strap 58 and a Velcro strap 60. The orthotic cuff 56, D-ring strap 58, and Velcro strap 60 may be considered together as an attachment mechanism for coupling the lower hinged assembly 16 to a leg of a user at an attachment site, which may be between an ankle and a knee of the leg of the user.

Each upright member 54 may be additionally coupled to a bearing 62 or joint proximate an opposing end portion from the orthotic cuff 56. The one or more bearings 62 may each be coupled to a sprocket 64. Each of the one or more bearings 62 may serve as a freely-rotating and load-bearing connection between the upright member 54 and the sprocket 64. Each collection of an upright member 54, a sprocket 64, and a bearing 62 may be operably coupled to one another through connecting hardware, such as bolts and nuts or other suitable connecting hardware. The connecting hardware may be disposed through various adjustment holes defined by the upright member 54 for adjustability of the lower hinged assembly 16 based on the user's body type.

In some embodiments, additional brackets are attached to the lower hinged assembly based on the joint that is to be assisted. For example, as illustrated in FIGS. 3-6, one or more insole brackets 66 may be rotatably coupled with the upright member 54. The insole brackets 66 support the foot of the user and received torque that is to be applied to a walking surface of the user. The one or more insole brackets 66 may be formed from a metallic material, a polymeric material, and/or any other suitable rigid material. The one or more insole brackets 66 may be configured to be inserted into a user's footwear using thin elements without external straps.

The cable sheaths 50 may be coupled to the lower hinged assembly 16 by lower barrel adjustors 68 to anchor the lower end portions thereof. The lower barrel adjustors 68 may provide adjustment of the length of the sheaths 50 thereby providing adjustment of the baseline tension of the extension cables 46 or contraction cables 48. The one or more barrel adjustors 68 may be mounted on a support block 70. The one or more support blocks 70 may each be additionally coupled to the upright member 54.

After passing through the barrel adjusters 68 and exiting their sheaths 50, the extension cables 46 and the contraction cables 48 may couple to the sprockets 64. The sprockets 64 may clamp to each of the extension cables 46 and the contraction cables 48 on a first end portion and coupled to a single actuator pulley 42 in the control unit 12 on a second end portion. In various embodiments, an opposing pair may instead embodied in a single element with the capability to transfer both positive and negative forces. In some embodiments, the sprocket 64 may include any device for capturing force from a transmission assembly 14 to produce torque between two or more attachment points with at least one attachment point on each side of a user's joint (e.g., torque between the insole bracket 66 and the orthotic cuff 56).

Each upright member 54 and insole bracket 66, taken in combination, may be considered as a force-applying arm applying torque around an axis. In some instances, the axis is generally aligned with a body joint axis (e.g. an ankle joint axis). When a force is applied along a length of extension cables 46 or contraction cables 48, a force is applied to sprocket 64 and, in turn, insole bracket 66. Accordingly, the forces applied along the lengths of extension cables 46 and contraction cables 48 apply a force causing insole bracket 66 to rotate about the bearing 62 with respect to upright member 54.

In various embodiments, the extension cables 46 and/or the contraction cables 48 can be actuated based on acquired data from one or more sensors 72 within the exoskeleton device 10 in reference to use of the hinged assembly. As provided herein, one or more performance metrics may be determine based on the acquired data, which may include at least one of a posture position, joint positions/angles, joint moment, joint power, or spatiotemporal parameters of walking, including step/stride length and gait speed. In some examples, the one or more sprockets 64 may each be additionally coupled to a torque sensor 74 or a joint angle encoder configured to measure an angle at some point during an individual's gait cycle as the data point. The torque sensor 74 may be used to sense the torque force applied by the exoskeleton device 10 for assistance. The torque sensor 74 may be additionally coupled to the insole bracket 66. In some embodiments, the one or more sprockets 64 may be coupled to the corresponding one or more insole brackets 66 without an intermediate torque sensor 74. Additionally or alternatively, in various embodiments, the sensor 72 may be configured as one or more accelerometers coupled the lower hinged assembly 16 to provide information on the user's gait.

In some embodiments, the sensor 72 may be configured as one or more pressure/force sensors 76 may also be operably coupled with the insole bracket 66. The one or more pressure/force sensors 76 may be positioned on an upwardly and/or a downwardly facing surface of the insole bracket 66 in various embodiments to provide spatial pressure information across the foot surface. The one or more pressure/force sensors 76 may include force-sensitive resistors, piezoresistors, piezoelectrics, capacitive pressure sensors, optical pressure sensors, resonant pressure sensors, or other means of sensing pressure, force, or motion.

The control unit containing the circuit board may include various electrical components for actuating one or more of the actuators 30. In turn, the actuators 30 provide force that is transmitted to one or more upper or lower hinged assemblies through the transmission assembly. In the embodiment illustrated in FIG. 7, the control unit 12 includes a controller 78 having a processor 80 and memory 82 that is powered by the power supply. Logic 84 is stored within the memory 82 and includes one or more routines that is executed by the processor 80, such as the method 106 described in reference to FIG. 10 and/or the method 120 described in reference to FIG. 11. The controller 78 includes any combination of software and/or processing circuitry suitable for controlling various components of the exoskeleton device 10 described herein including without limitation processors, microcontrollers, application-specific integrated circuits, programmable gate arrays, and any other digital and/or analog components, as well as combinations of the foregoing, along with inputs and outputs for transceiving control signals, drive signals, power signals, sensor signals, and so forth. All such computing devices and environments are intended to fall within the meaning of the term "controller" or "processor" as used herein unless a different meaning is explicitly provided or otherwise clear from the context.

Figure 7:
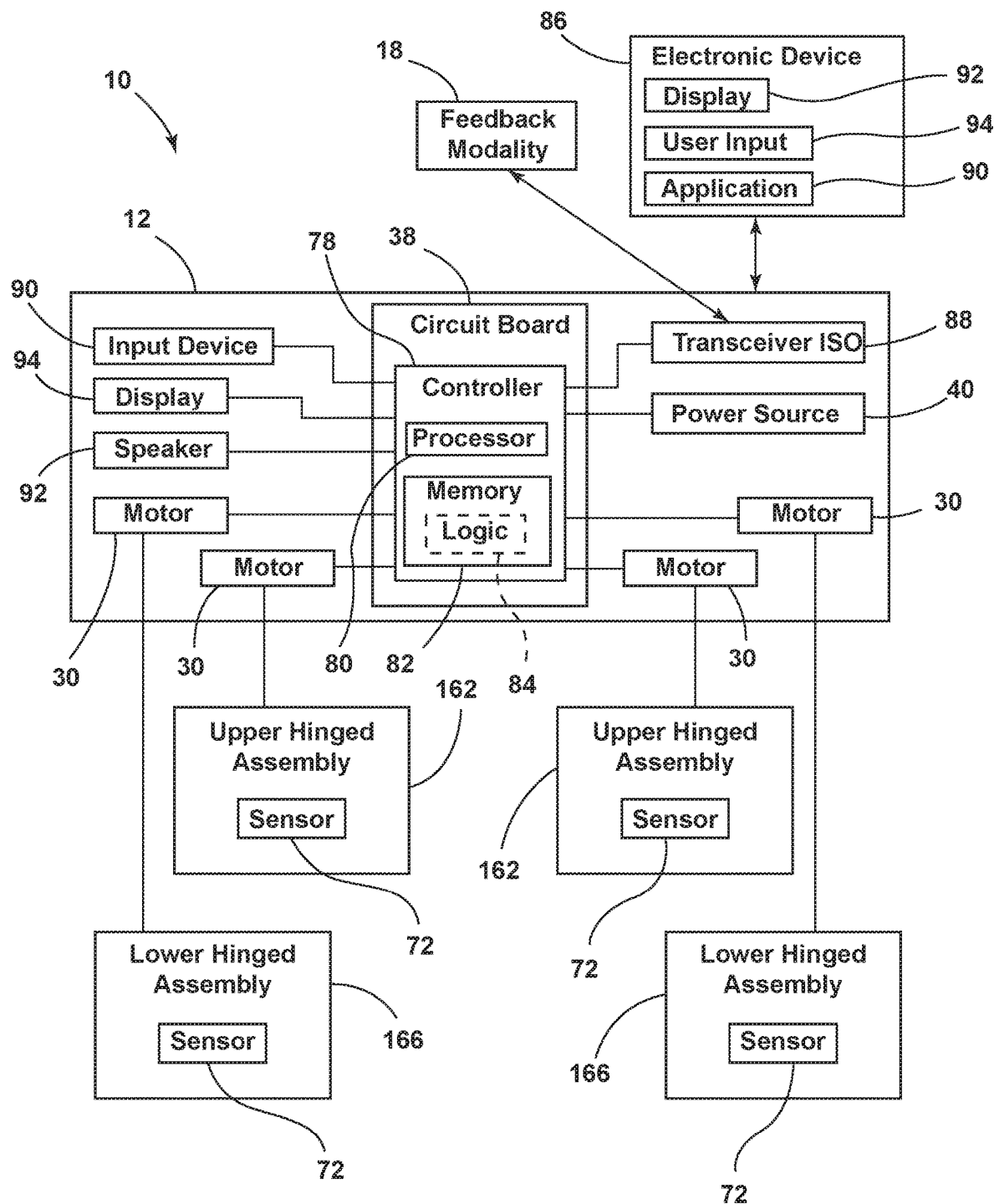
FIG. 7 is a block diagram of the exoskeleton device, according to some embodiments.

In some examples, more than one joint on a common limb may be assisted by the exoskeleton device and activated/deactivated by the controller. For example, in some instances, the exoskeleton device may provide assistance to any one or more of an ankle, a knee, and/or a hip of a user. In the embodiment of FIG. 7, the exoskeleton device 10 includes the control unit 12, a pair of upper hinged assemblies 16a and a pair of lower hinged assemblies 16b. The pair of upper hinged assemblies 16a may be positioned proximately to respective knees of a user while the lower hinged assemblies 16b may be positioned proximately to the user's respective ankles. In some examples, the exoskeleton device 10 may include any number of upper hinged assemblies 16a and/or lower hinged assemblies 16b depending on the assistance to be provided to the user.

In the embodiment illustrated in FIG. 7, the control unit 12 includes four actuators 30 that respectively control one of the upper and/or lower hinged assemblies 16a, 16b. In some embodiments, a first actuator 30 can provide a first level of assistance and the second actuator 30 can provide a second level of assistance. The first level of assistance can be greater than, equal to, or less than the second level of assistance during different phases in which the exoskeleton device 10 is used.

In some instances, a transmission may include various gear ratios that allow for more than one upper or lower hinged assembly 16a, 16b to be controlled by a common actuator 30. The actuators 30 may be disposed in an offset relationship from one another such that the transmission assemblies 14 extending from each of the actuators 30 towards the upper or lower hinged assemblies 16a, 16b and free of contact from one another within the control unit 12. It will be appreciated that the upper and lower hinged assemblies 16a, 16b illustrated in FIG. 7 may include any of the components described herein.

The control unit 12 may further include a display 94 for providing the status of the operation of the exoskeleton device 10 and/or operational data. The control unit 12 may further include an input device 90 for accommodating various user inputs and/or a speaker 92, which may also be operably coupled with the control unit 12, for notifying a user of any desired condition.

As provided herein, any of the upper and lower hinged assemblies 16a, 16b can include any type of sensor 72, which may communicate with the control unit 12 in a wired and/or wireless manner. For example, like the lower hinged assemblies 16b, the upper hinged assemblies 16a may also include a torque sensor 74. The torque sensor 74 may be used to sense the torque force applied by the exoskeleton device 10 for assistance. Additionally or alternatively, in various embodiments, one or more accelerometers may be coupled to the upper and/or lower hinged assemblies 16a, 16b to provide information on the user's gait. Additionally, angle sensors along the exoskeleton device 10 can measure various angles during a gait cycle and may include potentiometers, encoders (e.g., optical encoders), and the exoskeleton device 10 employing a light source and a light detector capable of calculating an angle of the exoskeleton device 10. Sensors such as inertial measurement units (IMUS) may also be used to determine acceleration, velocity, position, and orientations on one or more segments of the exoskeleton device 10 or biological limbs.

In some examples, the exoskeleton device 10 may communicate via wired and/or wireless communication with the feedback modality 18 and/or one or more handheld or electronic devices 86 through a transceiver 88. The communication may occur through one or more of any desired combination of wired (e.g., cable and fiber) and/or wireless communication mechanisms and any desired network topology (or topologies when multiple communication mechanisms are utilized). Exemplary wireless communication networks include a wireless transceiver 88 (e.g., a BLUETOOTH module, a ZIGBEE transceiver, a Wi-Fi transceiver, an IrDA transceiver, an RFID transceiver, etc.), local area networks (LAN), and/or wide area networks (WAN), including the Internet, cellular, satellite, microwave, and radio frequency, providing data point communication services.

The electronic device 86 may be any one of a variety of computing devices and may include a processor and memory. The memory may store logic having one or more routines that is executable by the processor. For example, the electronic device 86 may be a cell phone, computer, mobile communication device, key fob, wearable device (e.g., fitness band, watch, glasses, jewelry, wallet), apparel (e.g., a tee shirt, gloves, shoes or other accessories), personal digital assistant, headphones and/or other devices that include capabilities for wireless communications and/or any wired communications protocols. The electronic device 86 may have an application 91 thereon and a display 95 may provide a graphical user interface (GUI) and/or various types of information to a user. The operation of the various components of the exoskeleton device 10 may be altered through the usage of the application 91 and/or information regarding the operation of the components may be provided on the display 95. The electronic device 86 may likewise have any combination of software and/or processing circuitry suitable for controlling the exoskeleton device 10 described herein including without limitation processors, microcontrollers, application-specific integrated circuits, programmable gate arrays, and any other digital and/or analog components, as well as combinations of the foregoing, along with inputs and outputs for transceiving control signals, drive signals, power signals, sensor signals, and so forth.

In some embodiments, the electronic device 86 may be configured to receive user inputs via the input circuitry 93. For example, the inputs may relate to an amount of assistance to be provided by the exoskeleton device 10 or any other information and/or commands. In response, the controller 78 may activate/deactivate the one or more actuators 30 to produce force equating to the desired amount of assistance. Accordingly, usage of the exoskeleton device 10 may be varied through the usage of the application 91 in addition to or in lieu of usage of the input device 90. Additionally or alternatively, the electronic device 86 may also provide feedback information, such as visual, audible, and tactile alerts. The feedback information may be provided for any reason, including but not limited to, additional assistance being needed, less assistance being needed, a set number of cycles being reached, a predefined goal being accomplished, etc. The feedback information may be at least partially determined by the sensors 72, which may include by torque sensors 74, pressure/force sensors 76, and/or any other sensor within the exoskeleton device 10.

In some embodiments, the controller 78 operates a finite state machine to control the operation of the actuators 30 to provide assistance to a user. For example, the state machine implemented by the controller 78 may define a number of different states, including early stance, late stance, and swing phases of the user's gait or step cycle that, in turn, control which of the actuators 30 is operated to apply force to either extension cables 46 (FIG. 3) or contraction cables 48 (FIG. 3) to provide force assistance to the wearer. For example, when a pulling force is applied to a lower hinged assembly 16b by extension cables 46 through the actuators 30, a torque is applied to the sprocket 64 (FIG. 3) causing the insole bracket 66 (FIG. 3) to be rotated downwards with respect to the upright member 54 (FIG. 3) thereby assisting the user in moving their toes downwards (i.e., extension). Conversely, when a pulling force is applied to contraction cables 48 by actuators 30, a torque is applied to sprocket 64 causing the insole bracket 66 to be rotated upwards with respect to the upright member 54 thereby assisting the user in moving their toes upwards (i.e., contraction). In this manner, the upright member 54 and the insole bracket 66 operate as first and second arms of a hinged connection at the user's joint. The first arm of the hinge (e.g., the upright member 54) is fixed to the user's limb (e.g. by orthotic cuff 56 around the lower leg), while the second arm of the hinge (e.g., insole bracket 66) is positioned along a user's foot. Similarly, the actuators 30 may assist in extension and contraction of the upper hinged assembly 16b proximate to a user's knee to provide assistance to such joints during various portions of the gait cycle.

The state machine may receive input from one or more sensors 72, and use current and previous input values in order to determine a current state of the state machine. The current state is then used to determine the timing of the actuator 30 activation, in order to provide torque assistance to the user with appropriate timing and intensity (e.g., to provide extension assistance during toe-off, or contraction assistance during foot swing to prevent drop foot).

In some embodiments, the feedback modality 18 provides feedback regarding the individual's use of a wearable exoskeleton device 10 in a free-living environment. Various types of feedback mechanisms (e.g., auditory, visual, electro-tactile, vibro-tactile) and various locations of placement (e.g., leg, arm, torso, within the control unit 12) are suited for providing performance tracking during exoskeleton device 10 assisted walking. In some examples, the feedback modality 18 may include small vibratory actuators may be used to provide vibro-tactile feedback. Additionally or alternatively, the feedback modality 18 may include electrical stimulation that may be used to provide electro-tactile feedback. Additionally or alternatively, the feedback modality 18 may include an LED array or other visual display that may be used to provide color-coded visual feedback. Additionally or alternatively, the feedback modality 18 may include feedback utilizing one or more of wired or wireless (e.g., Bluetooth) headphones or a small piezo speaker that modulates a beep frequency to provide auditory signals to the individual. Each of the above feedback modalities may be used at logical body placements, which includes possible locations on the leg, hip, torso, and wrist. For example, vibro-tactile and electro-tactile feedback may be suitable for several different locations, while visual feedback may be suitable on locations that are easily seen by the individual user, such as the wrist.

In some embodiments, the controller 78 may provide instructions to a particular feedback modality 18 based on the input received from any of the embedded sensors 72. For example, the torque sensor 74 (or any other sensor) may be configured to measure an angle $\theta$ shown in FIG. 8 during the swing phase of an individual's gait. If the angle $\theta$ is not reaching the desired value, then the controller 78 activates a feedback modality 18 to inform the individual that they are not complying with the desired performance data point. The feedback modality 18 could include one or more of the various types of feedback described herein (tactile, visual, and auditory).

Additionally, compliance with a desired performance data point may also trigger a feedback modality 18 to inform the individual that they are indeed in compliance, or, the feedback modality 18 could inform the individual of both compliance and noncompliance. For example, if, in the above example, the modality contains both green and red light sources, the green light source is illuminated if the angle $\theta$ reaches the desired value, and the red light source is illuminated if the angle $\theta$ is does not reach the desired value. Electromyography may be used to measure the compliance of specific muscles or muscle groups and relay this information through the feedback modality 18. Likewise, the feedback modality 18 may provide a first sound from a speaker or within the control unit 12 or the feedback modality 18 when a user is in compliance with the performance data point and a second sound when the user is not in compliance with the performance data point. Additionally, sounds may be generated when other conditions are obtained and/or are not obtained.

The feedback modality may also be used in combination with gamification to enhance the experience of gait rehabilitation and to further engage and incentivize the individual with the feedback process. Non-limiting examples include a scoring system based on collecting points, coins, or other rewards based on rehabilitation progress customized to the individual. The application on the electronic device may be designed to allow the individual to play outside of the rehabilitation setting. The application may also be connected to an individual's physical therapist's (or other advisor's) database or electronic device to report progress or may connect to other systems for using the exoskeleton device in a social or competitive context. For example, in the example illustrated in FIG. 9, the exoskeleton device 10, the electronic device 86, and/or the feedback modality 18 may be communicatively coupled with one or more remote sites such as a remote server 96 via a network/cloud 98.

The network/cloud 98 represents one or more systems by which the exoskeleton device 10, the electronic device 86, and/or the feedback modality 18 may communicate with the remote server 96. Accordingly, the network/cloud 98 may be one or more of various wired or wireless communication mechanisms, including any desired combination of wired and/or wireless communication mechanisms and any desired network topology (or topologies when multiple communication mechanisms are utilized). Exemplary communication networks 172 include wireless communication networks (e.g., using Bluetooth, IEEE 802.11, etc.), local area networks (LAN) and/or wide area networks (WAN), including cellular networks, satellite networks, microwave networks, radio frequency networks, the Internet and the Web, which all may provide database communication services and/or cloud computing services.

The Internet is generally a global database communications system that is a hardware and software infrastructure, which provides connectivity between computers. In contrast, the Web is generally one of the services communicated via the Internet. The Web is generally a collection of interconnected documents and other resources, linked by hyperlinks and URLs. In many technical illustrations when the precise location or interrelation of Internet resources are generally illustrated, extended networks such as the Internet are often depicted as a cloud (e.g. 98 in FIG. 9). The verbal image has been formalized in the newer concept of cloud computing. The National Institute of Standards and Technology (NIST) provides a definition of cloud computing as "a model for enabling convenient, on-demand network access to a shared pool of configurable computing resources (e.g., networks, servers, storage, applications, and services) that can be rapidly provisioned and released with minimal management effort or service provider interaction." Although the Internet, the Web, and cloud computing are not exactly the same, these terms are generally used interchangeably herein, and they may be referred to collectively as the network/cloud 98.

The server 96 may be one or more computer servers, each of which may include at least one processor and at least one memory, the memory storing instructions executable by the processor, including instructions for carrying out various steps and processes. The server 96 may include or be communicatively coupled to a data store 100 for storing collected data point as well as instructions for operating the exoskeleton device 10, the feedback modality 18, the electronic device 86, etc. that may be directed to and/or implemented by the exoskeleton device 10, the electronic device 86, and/or the feedback modality 18 with or without intervention from a user and/or the electronic device 86.

In some examples, the instructions may be inputted through the electronic device 86 and relayed to the server 96. Those instructions may be stored in the server 96 and/or data store 100. At various predefined periods and/or times, the exoskeleton device 10 and/or the feedback modality 18 may communicate with the server 96 through the network/cloud 98 to obtain the stored instructions, if any exist. Upon receiving the stored instructions, the exoskeleton device 10 and/or the feedback modality 18 may implement the instructions. The server 96 may additionally store information related to multiple exoskeleton devices 10 and operate and/or provide instructions to the exoskeleton device 10, the feedback modality 18, and the electronic device 86 in conjunction with the stored information with or without intervention from a user. The information may include performance data point from a wide array of users.

Figure 8:
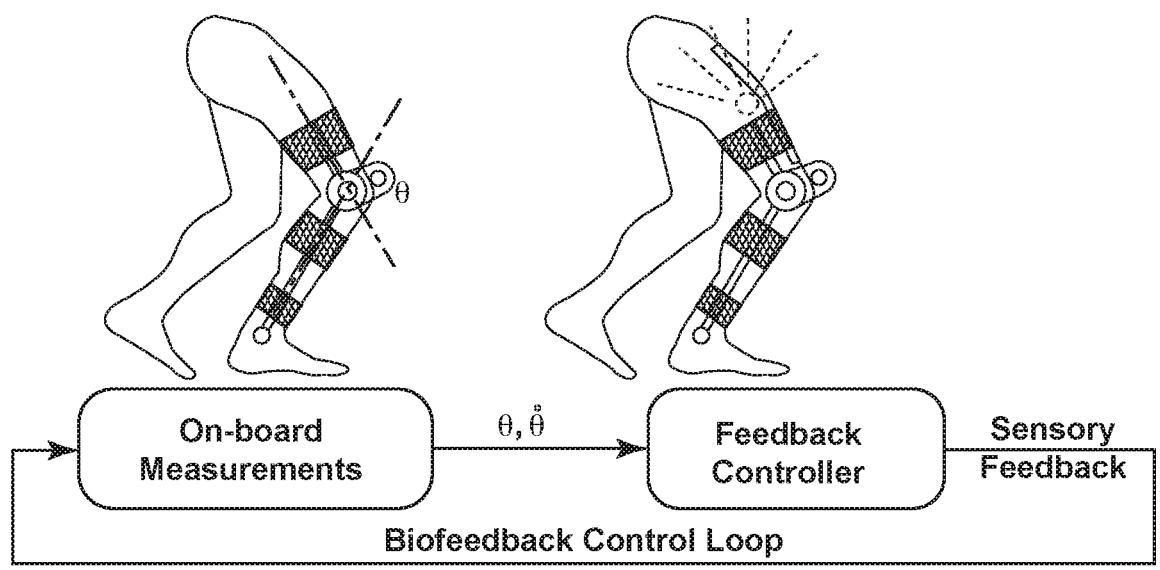
FIG. 8 is a diagram illustrating a knee joint angle that may be measured through the usage of the exoskeleton device, according to some embodiments.

With further reference to FIG. 8, the server 96 also generally implements features that may enable the exoskeleton device 10 and/or the feedback modality 18 to communicate with cloud-based applications 102. Communications from the exoskeleton device 10 and/or the feedback modality 18 can be directed through the network/cloud 98 to the server 96 and/or cloud-based applications 102 with or without a networking device 104, such as a router and/or modem. Additionally, communications from the cloud-based applications 102, even though these communications may indicate one of the exoskeleton device 10 and/or the feedback modality 18 as an intended recipient, can also be directed to the server 96. The cloud-based applications 102 are generally any appropriate services or applications 102 that are accessible through any part of the network/cloud 98 and may be capable of interacting with the exoskeleton device 10 and/or the feedback modality 18.

In various examples, the electronic device 86 can be feature-rich with respect to communication capabilities, i.e. have built-in capabilities to access the network/cloud 98 and any of the cloud-based applications 102 or can be loaded with, or configured to have, such capabilities. The electronic device 86 can also access any part of the network/cloud 98 through wired or wireless access points, cell phone cells, or network nodes. In some examples, users can register to use the remote server 96 through the electronic device 86, which may provide access the exoskeleton device 10 and/or the feedback modality 18 and/or thereby allow the server 96 to communicate directly or indirectly with the exoskeleton device 10 and/or the feedback modality 18. In various instances, the exoskeleton device 10 and/or the feedback modality 18 may also communicate directly, or indirectly, with the electronic device 86 or one of the cloud-based applications 102 in addition to communicating with or through the server 96. According to some examples, the exoskeleton device 10 and/or the feedback modality 18 can be preconfigured at the time of manufacture with a communication address (e.g. a URL, an IP address, etc.) for communicating with the server 96 and may or may not have the ability to upgrade or change or add to the preconfigured communication address.

Figure 9:
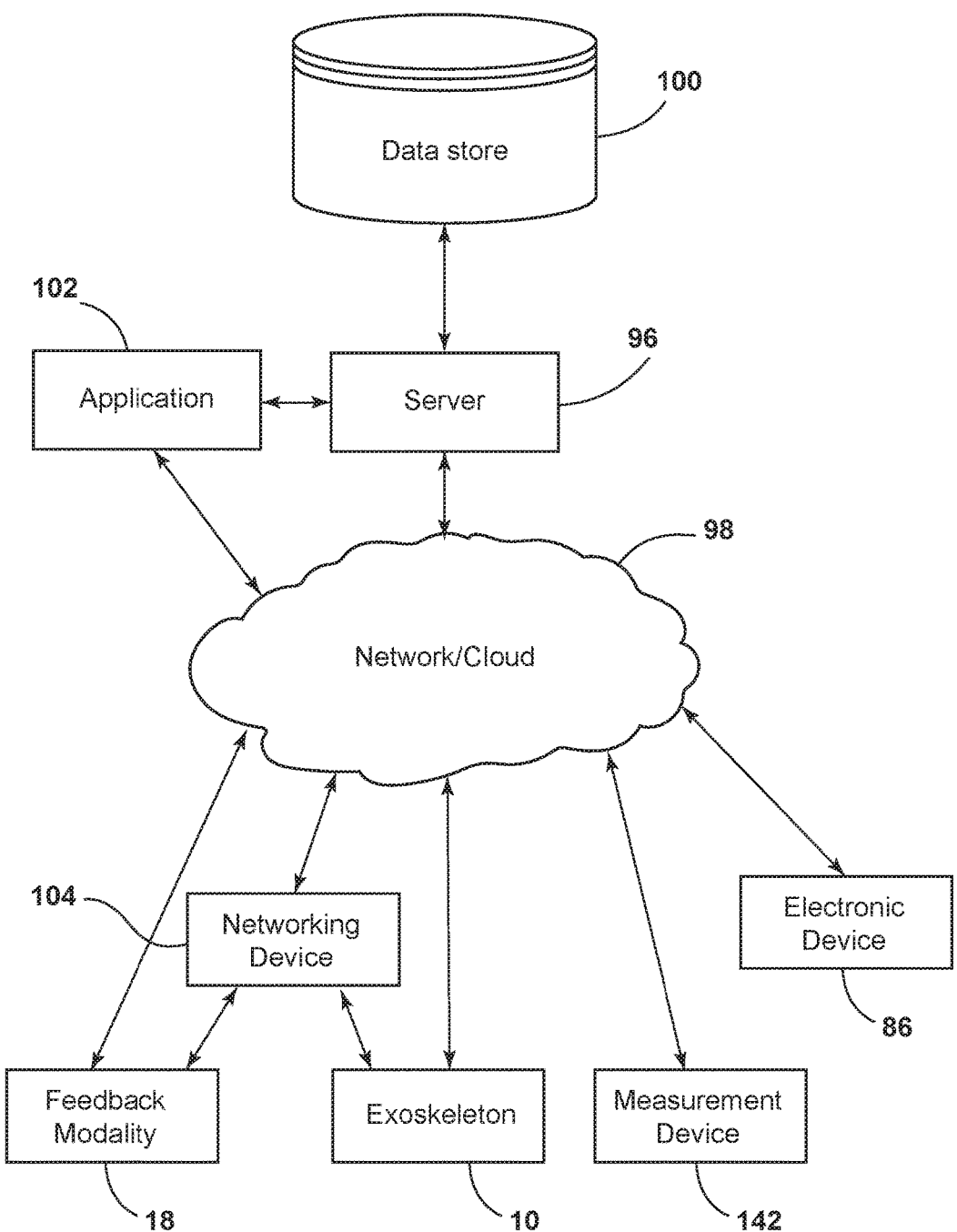
FIG. 9 is a block diagram of the exoskeleton device communicatively coupled with various other devices through a network/cloud, according to some embodiments.

Referring still to FIG. 9, when a new cloud-based application 102 is developed and introduced, the server 96 can be upgraded to be able to receive communications for the new cloud-based application 102 and to translate communications between the new protocol and the protocol used by the exoskeleton device 10 and/or the feedback modality 18. The flexibility, scalability, and upgradeability of current server technology render the task of adding new cloud-based application protocols to the server 96 relatively quick and easy.

In some examples, wearable assistance system includes the exoskeleton device 10, the feedback modality 18, the electronic device 86, and/or a measurement device. The measurement device is configured to generate biomechanical data point of an individual. The collected data point can then be used to determine an individual's gait deficits. The controller 78 of the exoskeleton is configured to actuate the actuator 30 at an initial level of assistance based on the gait deficits. In various examples, the measurement device is a motion capture camera configured to detect movement and force gait analysis. Additionally or alternatively, the measurement device utilizes a measurement of muscle activity through electromyography. Additionally or alternatively, the measurement device utilizes a measurement of oxygen consumption/$CO_2$ production to determine a metabolic rate. The generated biomechanical data point of the individual can be compared to a computer-generated model of a gait cycle.

Figure 10:
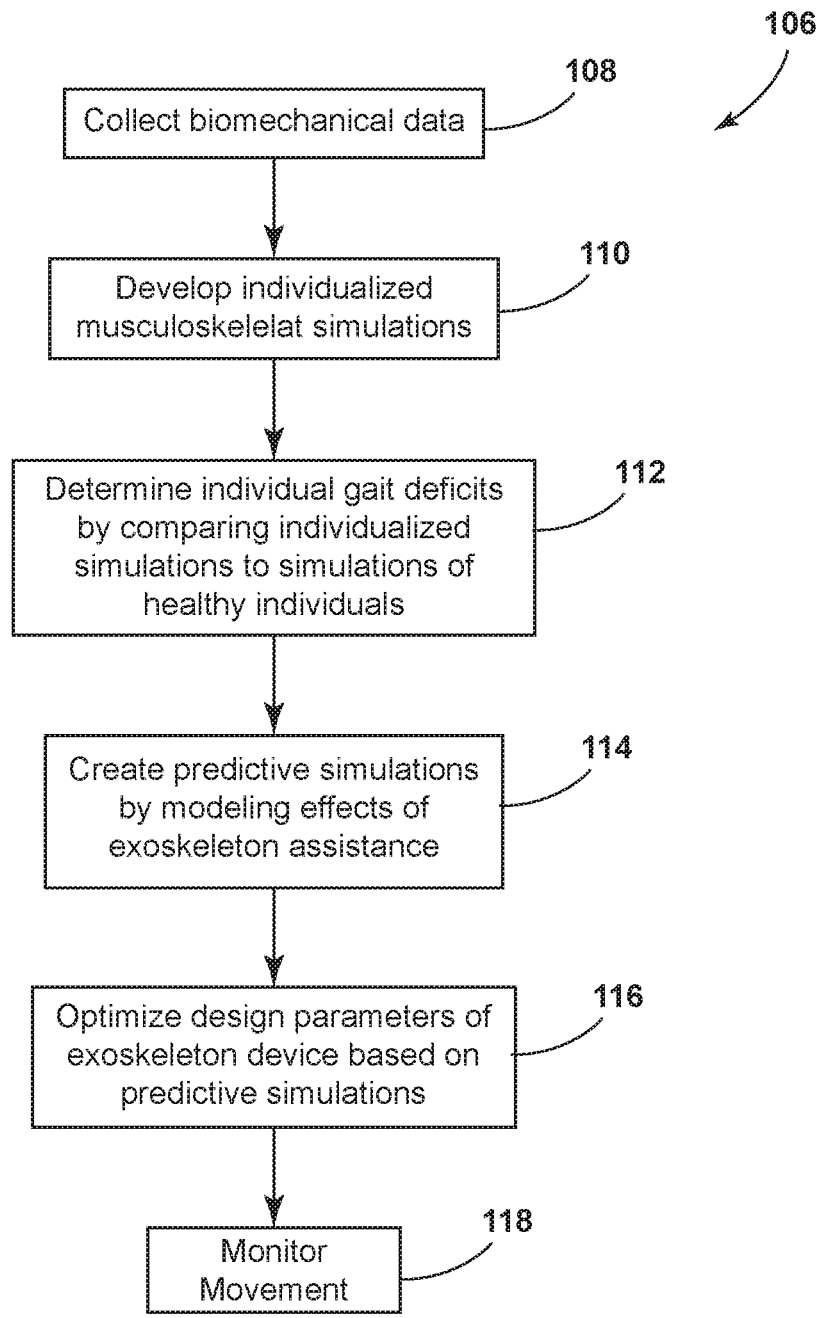
FIG. 10 is a flowchart of a method of optimizing design parameters of the exoskeleton device, according to various embodiments.

In some embodiments, a method of initially defining a musculoskeletal model may be used to help inform the design of personalized assistive devices. The computer-generated musculoskeletal model is based on the results obtained by any one or more of a detailed biomechanical, gait, and neuromuscular assessment of an individual. For example, as illustrated in FIG. 10, a method 106 begins at step 108, in which biomechanical data point is collected. As non-limiting examples, the collection of the biomechanical data point can be performed in a laboratory or rehabilitation setting and utilizing a measurement device motion capture of movement and force gait analysis via motion capture cameras, a measurement of muscle activity through electromyography, and/or a measurement of oxygen consumption/$CO_2$ production to determine a metabolic rate. Accordingly, one or more of wearable sensors (joint encoders for angle measurement, embedded shoe sensors for ground reaction force measurement, etc.), a motion capture camera (movement and force gait analysis via motion capture cameras); a measurement device for monitoring muscle activity (electromyography, EMG, wireless electromyography electrodes); a neuromuscular assessment device (balance testing device and dynamometer); a measurement device of oxygen consumption/$CO_2$ production (metabolic rate); and/or any other practicable device can be used during the collection of the biomechanical data point. Based on the data point collected, an individual that would benefit from a wearable robotic assistance device is evaluated.

During the data point collection, the individual may perform a series of activities with or without the exoskeleton, including, for example, walking on a treadmill while being filmed with the motion capture cameras and having their muscle activity and oxygen consumption measured. The individual may also undergo a neuromuscular assessment. This baseline analysis of an individual's gait and motion estimates the muscle forces in either a total sum of muscle forces or single muscles, modeled as individual lines of action.

Based on the biomechanics data point collected at step 108, an individualized musculoskeletal (computer-generated) simulation is developed for each individual in order to inform the design of the personalized assistive devices at step 110. In some embodiments of the method illustrated in FIG. 10, each individual's gait deficits and the contributing mechanisms are determined by comparing the results of the individualized musculoskeletal simulations to simulations of healthy individuals at step 112. The comparative data point may be generated during data point collection on other individuals within the lab and/or through data point compilation of the exoskeleton device 10 usage by other individuals that is stored/obtained through the network/cloud 98. In such instances, the data point may be dynamically updated based on the addition of new data point. However, in some embodiments, step 112 may be replaced by a computer-generated model or not needed altogether.

Next, at step 114, predictive simulations are created by modeling the effects of exoskeleton device assistance on the individualized simulations to inform the design and control of each individual's exoskeleton device 10. The predictive simulation provides an initial forecast of the individual's gait with the exoskeleton device assistance. In some instances, this simulation can significantly reduce the individual's customization time, which may be beneficial as many patients may be easily exhausted by testing and adjustment of the exoskeleton device 10.

The predictive simulations of step 114 provide the optimized design parameters, which at step 116 are implemented in the individualized robotic wearable exoskeleton device 10. The optimized design parameters set an initial assistance level at each hinged assembly 16 for the user of the exoskeleton device 10. Thus, the wearable assistance provided via the exoskeleton device 10 is tailored to the specific gait deficits of each individual. The exoskeleton device 10 can provide a small, calculated amount of electronic assistance that is intended to augment existing muscle activity to elicit functional changes at the hip, knee, or ankle joints.

While assisting the user during the gait cycle, the user may still experience instability. Accordingly, in various embodiments, the exoskeleton device 10 also may implement safety precautions to assist in patient safety, including, mechanical "stops" to prevent hyperextension of joints, an emergency stop button that shuts off power to the device, and embedded software mechanisms that shut off power if the user were to fall. The safety precautions may also be connected to the network/cloud 98.

At step 118, the movement of an individual may be monitored to determine if appropriate assistance is being provided. In some embodiments, the monitoring is accomplished through the sensors 72 embedded within the exoskeleton. Additionally and/or alternative, the monitoring may be accomplished through sensors that are remote to the exoskeleton device 10.

In some embodiments, the amount of assistance a user may need may increase or decrease over time. For example, as a disease continues, the amount of mobility of a user may decrease, thus, they may need increased assistance. On the other hand, in some situations, with or without the use of the exoskeleton device 10, a user may be able to improve their mobility or strength, thus, may need less assistance over time. Accordingly, the controller can be configured to decrease the level of assistance or increase resistance when the change in the at least one data point is indicative of increased performance by an individual using the exoskeleton device. Conversely, the controller can be configured to increase the level of assistance or decrease resistance when the change in the at least one data point is indicative of decreased performance by an individual using the exoskeleton device. To account for possible changes in assistance, an exoskeleton device control algorithm capable of establishing and tracking personalized measures of exoskeleton device 10 assisted walking performance may be present within the control unit 12 (see FIG. 9) and/or located in the server 96, which may be accessed through the network/cloud 98. In the example shown in FIG. 11, a hierarchical control strategy is programmed onto the memory (FIG. 7). As provided herein, the control strategy utilizes data point from one or more sensors 72 embedded in the exoskeleton device 10 to track posture and/or other data points, evaluate how these data points change over time and adjust the level of assistance accordingly.

Figure 11:
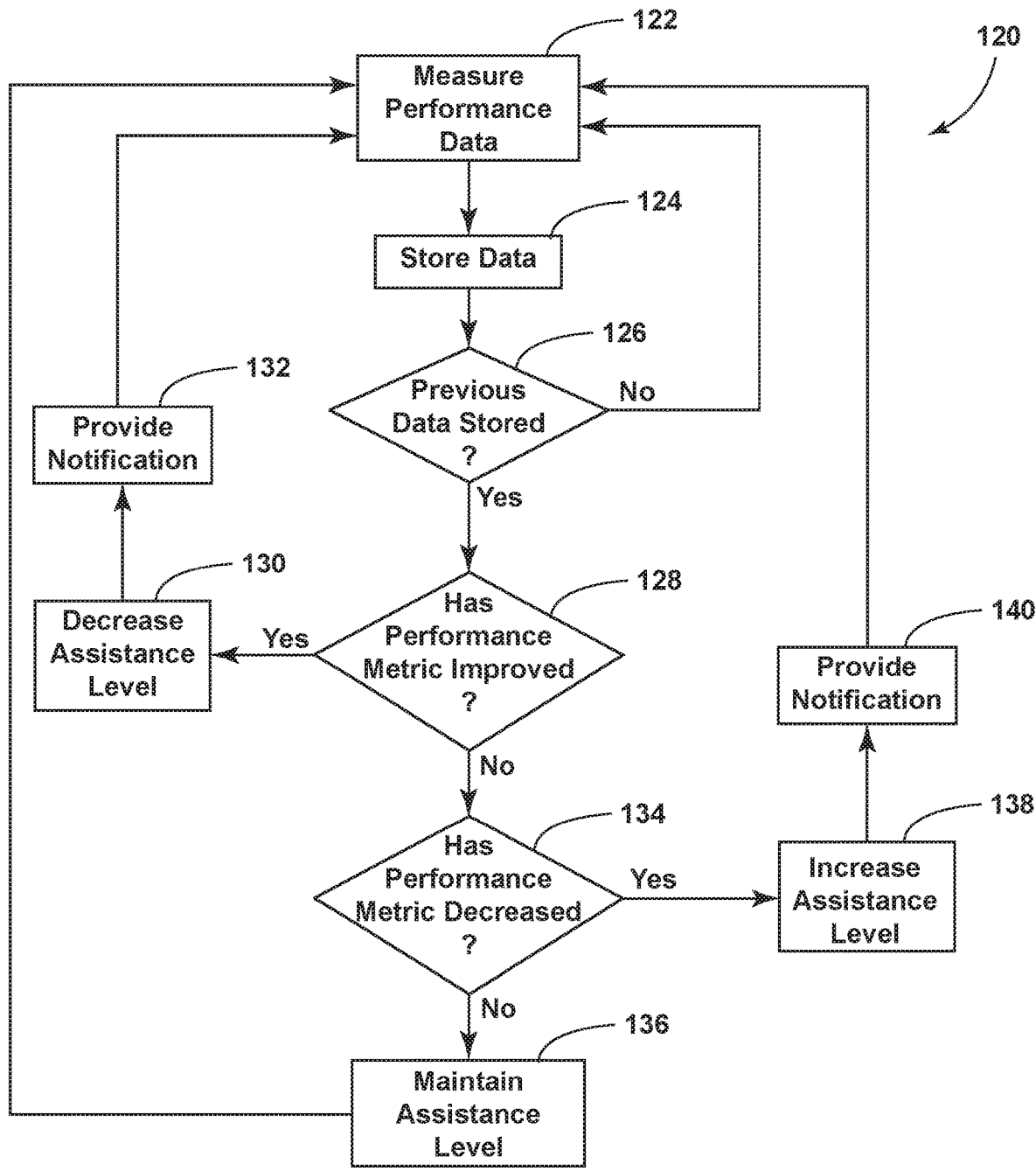
FIG. 11 is a flowchart of a method of dynamically (intermittently) updating a level of assistance provided by the exoskeleton device based on a sensor data point, according to some embodiments.

For example, in the embodiment illustrated in FIG. 11, an example of a closed loop method 120 for adaptively altering an amount of assistance is provided. In the embodiment illustrated in FIG. 11, the method begins at step 122, in which a user's performance is measured by the one or more sensors 72 embedded within the exoskeleton device 10. In various examples, the one or more sensors 72 can be incorporated at the lower hinged assembly 16a (FIG. 7) of the exoskeleton device 10 to measure the forces being applied to the foot, at the upper hinged assembly 16b (FIG. 7) to measure a degree of rotation of the knee through the gait cycle, and/or at the hip to measure the kinematics of the hip joint through the gait cycle. These measurements can be used to determine the stance versus swing phase of the walking motion. Depending on the specific gait deficit of the individual, the exoskeleton device 10 may include one or more types of sensors 72 and/or one or more of the same type of sensor 72.

At step 124, the measured data point is stored in the memory of the control unit 12, in the data store 100 that is remote from the exoskeleton device 10, and/or in the electronic device 86. The stored data point may be retained in any manner. The stored data point may be accessed by the control unit 12 of the exoskeleton device 10, the feedback modality 18, and/or a remote electronic device 86. The remote electronic device 86 may be accessed by a remote advisor, such as a physical therapist, who can, in turn, monitor the usage of the exoskeleton device 10 and/or adjust the assistance level provided by the exoskeleton device 10 remotely. In addition, the electronic device 86 may also be a database that compiles the stored data point from one or more users that can be used for a wide array of analyses and adjustments in assistance levels.

At step 126, the method determines if measurement data point regarding a specific user has previously been stored. If no data point has previously been stored, the method returns to step 122 and measures additional performance data point. If previous data point has been stored, the method continues to step 128 in which the most recently collected data point is compared to previously obtained data point to determine when a performance metric has increased. To determine a performance metric, any of the data points collected by the exoskeleton device 10 may be used. In some embodiments, the most recently obtained data point may be compared to a predefined number of previous cycles. For example, the most recent data point may be compared to 100 (or any other number of) previous data point acquisition cycles. The comparisons may be used to define trends, which in turn, may be used to determine a prolonged performance trend of the user. The prolonged performance trend may be used for determining whether to adjust the assistance level of the exoskeleton device 10.

If the performance metric of the user has increased, the method continues to step 130 in which the amount of assistance or resistance provided by the exoskeleton device 10 is adjusted (increased or decreased). In some embodiments, the method continues to step 132 wherein a notification is provided to the user that their performance has increased by at least a threshold amount, and thus, the amount of assistance provided will be reduced. The method may then continue back to step 122 to collect the next iteration of data point.

If at step 128 it is determined that the performance metric hasn't improved by at least a threshold level, the method continues to step 134, where the method determines whether the performance data point has decreased by a threshold amount. If the performance data point has not decreased by a threshold amount, then the method continues to step 136 where the amount of assistance or resistance provided is maintained. Next, the method returns to step 122 where an additional cycle of data point is collected.

If at step 136 it is determined that the performance metric has fallen below the threshold level, the method continues to step 138 wherein the amount of assistance provided by the exoskeleton device 10 is increased. Next, the method can continue to step 140, where a notification is provided to the user and/or another person that the performance data point has fallen and that additional assistance or resistance will be administered. The method then returns to step 122 to collect additional data point.

Accordingly, as a non-limiting example of the method, a sensor 72 may measure the angle θ during the swing phase of an individual's gait. If the angle θ is not reaching the desired value at a certain level of assistance, then the controller 78 instructs the actuator 30 to increase assistance. Conversely, if the angle θ is consistently reaching the desired value at a given level of assistance, then the controller 78 instructs the actuator 30 to gradually decrease the assistance level. If the performance metric is being met within upper and lower bands, the assistance level provided by the exoskeleton device 10 may be maintained.

Use of the present disclosure may offer a variety of advantages, which is provided by various combinations of the features provided herein. For example, the exoskeleton device provided herein may provide assistance to any number of joints of a user. Moreover, the assistance or resistance may be provided in a real-world environment, versus just in a lab. The exoskeleton may be minimally invasive to the user during day-to-day activities and manufactured at substantially reduced costs compared to various other assistance devices that are commercially available. The exoskeleton may provide assistance during some modes of operation specifically intended to improve mobility or posture. Additionally or alternatively, the exoskeleton may provide resistance a mode of operation designed to increase muscle recruitment during a function task (e.g. walking). The exoskeleton provided herein may be coupled with a feedback modality that allows for feedback regarding use of the exoskeleton device. For example, the user modality may alert a user when various performance goals are met. In addition, the exoskeleton may be remotes coupled to an electronic device. The electronic device may obtain data regarding the exoskeleton device and/or provided controls for altering usage of the exoskeleton device. In addition, the exoskeleton device may include one or more algorithms for intermittently adjusting the assistance level of the exoskeleton device based on the user performance. The assistance level may be changed from an initial assistance level that is obtained through various methods provided herein that make it quicker and more obtainable for a user with gait deficits to be fitted with the exoskeleton device.

It will be understood by one having ordinary skill in the art that construction of the described invention and other components is not limited to any specific material. Other exemplary examples of the invention disclosed herein may be formed from a wide variety of materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

Furthermore, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably couplable" to each other to achieve the desired functionality. Some examples of operably couplable include, but are not limited to, physically mateable, physically interacting components, wirelessly interactable, wirelessly interacting components, logically interacting, and/or logically interactable components.

It is also important to note that the construction and arrangement of the elements of the invention as shown in the examples are illustrative only. Although only a few examples of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system might be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary examples without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting. In addition, variations and modifications can be made on the aforementioned structures and methods without departing from the concepts of the present invention and such concepts are intended to be covered by the following claims unless these claims by their language expressly state otherwise.

What is claimed is:

1. A method of using an ankle exoskeleton device, the method comprising:
    collecting one or more biomechanical data points from an individual using wearable sensors or sensors embedded within the exoskeleton device;
    developing individualized musculoskeletal simulations based on the one or more biomechanical data points;
    creating predictive simulations by modeling effects of an ankle exoskeleton device on the individualized musculoskeletal simulations;
    determining gait deficits by comparing the results of the individualized musculoskeletal simulations to data points collected on other individuals using the exoskeleton device; and
    determining a control algorithm configured to modify an operation of the exoskeleton device based on the predictive simulations and the gait deficits.

2. The method of claim 1, wherein the control algorithm utilizes data point from an embedded sensor on the exoskeleton device to track at least one data point, evaluates how the at least one data point changes over time, and adjusts a level of assistance provided by the exoskeleton device.

3. The method of claim 1, wherein determining the control algorithm based on the predictive simulations further comprises:
    augmenting, using the control algorithm, existing muscle activity to elicit functional changes of the individual through activation of one or more actuators.

4. The method of claim 1, further comprising:
    assisting the individual during a gait cycle through manipulation of the exoskeleton device.

5. The method of claim 1, further comprising:
    resisting the individual during a gait cycle through manipulation of the exoskeleton device.

6. A wearable assistance system, comprising:
    an ankle exoskeleton device comprising:
        a control unit including a controller; and
        a motor in electrical communication with the controller; and
    a measurement device configured to generate biomechanical data points of an individual, wherein the measurement device is configured to determine an individual's gait deficits by developing individualized musculoskeletal simulations based on the biomechanical data points and comparing the results of the individualized musculoskeletal simulations to data points collected on other individuals using the exoskeleton device and the controller is configured to actuate the motor at an initial level of assistance based on the gait deficits.

7. The wearable assistance system of claim 6, wherein the generated biomechanical data point of the individual is compared to a computer-generated model of a gait cycle.

8. The wearable assistance system of claim 6, wherein the measurement device is a motion capture camera configured to detect movement.

9. The wearable assistance system of claim 6, where the measurement device utilizes a measurement of muscle activity through electromyography.

10. The wearable assistance system of claim 9, wherein the actuator is operably coupled to a hinged assembly through a transmission assembly and configured to actuate the hinged assembly when the actuator is activated by the controller.

11. The wearable assistance system of claim 10, wherein the hinged assembly includes an insole bracket rotatably coupled with an upright member.

12. The wearable assistance system of claim 6, where the measurement device utilizes a measurement of oxygen consumption/CO2 production to determine a metabolic rate.

13. A method of using an ankle exoskeleton device, the method comprising:
    collecting one or more biomechanical data points from an individual;
    developing individualized musculoskeletal simulations based on the one or more biomechanical data points;
    utilizing established biomechanical relationships governing an interaction between the device and the individual to create predictive simulations by modeling effects of the ankle exoskeleton device on the individual musculoskeletal simulations;
    determining gait deficits by comparing the results of the individualized musculoskeletal simulations to data points collected on other individuals using the exoskeleton device; and
    modifying a control system of the exoskeleton device based on the predictive simulations and the gait deficits.

14. The method of using an ankle exoskeleton device of claim 13, wherein the collecting one or more biomechanical data points from an individual includes utilizing motion capture of movement and force gait analysis via motion capture cameras or utilizing on-board device sensors.

15. The method of using an ankle exoskeleton device of claim 13, wherein the collecting one or more biomechanical data points from an individual includes utilizing a measurement of muscle activity through electromyography.

16. The method of using an ankle exoskeleton device of claim 13, wherein the collecting one or more biomechanical data points from an individual includes utilizing a measurement of oxygen consumption/$CO_2$ production to determine a metabolic rate.

\* \* \* \* \*